(12) United States Patent
Schroeder et al.

(10) Patent No.: US 10,835,467 B2
(45) Date of Patent: Nov. 17, 2020

(54) STABILIZING MIXTURE

(71) Applicant: Henkel AG & Co. KGaA, Duesseldorf (DE)

(72) Inventors: Thomas Schroeder, Hamburg (DE); Dirk Hentrich, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 46 days.

(21) Appl. No.: 15/742,885

(22) PCT Filed: Apr. 26, 2016

(86) PCT No.: PCT/EP2016/059221
§ 371 (c)(1),
(2) Date: Jan. 9, 2018

(87) PCT Pub. No.: WO2017/012727
PCT Pub. Date: Jan. 26, 2017

(65) Prior Publication Data
US 2018/0207072 A1    Jul. 26, 2018

(30) Foreign Application Priority Data

Jul. 17, 2015 (DE) .................. 10 2015 213 478

(51) Int. Cl.
| | | |
|---|---|---|
| *A61K 8/04* | (2006.01) | |
| *A61K 8/44* | (2006.01) | |
| *A61K 8/46* | (2006.01) | |
| *A61Q 19/10* | (2006.01) | |
| *A61K 8/92* | (2006.01) | |
| *A61K 8/42* | (2006.01) | |
| *A61Q 19/00* | (2006.01) | |
| *A61Q 5/02* | (2006.01) | |
| *A61K 8/86* | (2006.01) | |

(52) U.S. Cl.
CPC .................. *A61K 8/44* (2013.01); *A61K 8/04* (2013.01); *A61K 8/42* (2013.01); *A61K 8/463* (2013.01); *A61K 8/86* (2013.01); *A61K 8/922* (2013.01); *A61Q 5/02* (2013.01); *A61Q 19/00* (2013.01); *A61Q 19/10* (2013.01); *A61K 2800/436* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 4,865,774 A | | 9/1989 | Fabry et al. |
| 4,931,218 A | | 6/1990 | Schenker et al. |
| 5,294,726 A | | 3/1994 | Behler et al. |
| 5,312,932 A | | 5/1994 | Behler et al. |
| 5,322,957 A | | 6/1994 | Fabry et al. |
| 5,484,531 A | | 1/1996 | Kuehne et al. |
| 6,235,913 B1 | | 5/2001 | Raths et al. |
| 6,727,217 B1 | | 4/2004 | Nieendick et al. |
| 2005/0130865 A1 | | 6/2005 | Schmid et al. |
| 2009/0169644 A1 | | 7/2009 | Goddinger et al. |
| 2014/0023606 A1 | * | 1/2014 | Scheunemann .......... A61Q 5/02 424/70.13 |
| 2014/0348927 A1 | | 11/2014 | Schroeder et al. |

FOREIGN PATENT DOCUMENTS

EP      1977728 A2    10/2008

OTHER PUBLICATIONS

EPO, International Search Report and Written Opinion issued in International Application No. PCT/EP2016/059221, dated Jun. 30, 2016.
Ahmed, Fahim U., "Efficient Synthesis of Fatty Monoglyceride Sulfates from Fatty Acids and Fatty Acid Methyl Esters", JAOCS, vol. 67, No. 1, Jan. 1990, pp. 8-11.
Biswas, A. K. et al., "Surface-Active Properties of Sodium Salts of Sulfated Fatty Acid Monoglycerides", The Journal of the American Oil Chemists' Society, vol. 37, Apr. 1960, pp. 171-175.

* cited by examiner

*Primary Examiner* — Jessica Worsham
(74) *Attorney, Agent, or Firm* — Lorenz & Kopf, LLP

(57) ABSTRACT

The present disclosure relates to a stabilization mixture, i.e. a finely distributed dispersion of hydrogenated castor oil in water with anionic, amphoteric and nonionic surfactants which is suitable for stabilizing the pearlescence of surfactant agents, particularly cosmetic agents. Furthermore, the present disclosure relates to a cold process for producing surfactant-containing agents having a pearlescent effect, in particular cosmetic cleaning agents having a pearlescent effect, and to the use of the stabilizing mixture for stabilizing surfactant agents containing pearlescent waxes and/or pearlescent pigments containing surfactant agents.

13 Claims, No Drawings

STABILIZING MIXTURE

CROSS-REFERENCE TO RELATED APPLICATION

This application is a U.S. National-Stage entry under 35 U.S.C. § 371 based on International Application No. PCT/EP2016/059221, filed Apr. 26, 2016 which was published under PCT Article 21(2) and which claims priority to German Application No. 10 2015 213 478.4, filed Jul. 17, 2015, which are all hereby incorporated in their entirety by reference.

TECHNICAL FIELD

The present disclosure relates to a stabilization mixture, i.e. a finely distributed dispersion of hydrogenated castor oil in water with anionic, amphoteric and nonionic surfactants which is suitable for stabilizing the pearlescence of surfactant agents, particularly cosmetic agents. Furthermore, the present disclosure relates to a cold process for producing surfactant-containing agents having a pearlescent effect, in particular cosmetic cleaning agents having a pearlescent effect, and to the use of the stabilizing mixture for stabilizing surfactant agents containing pearlescent waxes and/or pearlescent pigments containing surfactant agents.

BACKGROUND

The manufacturers of cosmetic preparations attempt to give their products an attractive, valuable and rich appearance by employing pearlescence. For modern cosmetics, pearlescent waxes, in particular of the type of the glycol monofatty and difatty acid esters, are of importance, for example, stearates, which are used, for example, for producing pearlescence in hair shampoos and shower gels. Pigments such as titanium dioxide, iron oxides or mica are also used for imparting pearlescence in cosmetic agents. In the end product, these pearlescent substances are stabilized in an anionically based matrix, and ideally in such a manner that a fine and homogeneous distribution of the pearlescent substances is present and this state is also maintained under normal storage conditions.

Commercially available pearlescent waxes have melting points above about 80° C. and can therefore not be incorporated cold into aqueous formulations. The person skilled in the art is therefore generally forced to work according to a hot process in the production of surfactant agents having a pearlescent effect, i.e. to melt the waxes and to slowly crystallize it in the formulation, wherein the fineness of the crystals and thus the brilliance of the pearlescence is a function of the cooling rate. Such methods are time-consuming and energy-intensive. Furthermore, with this production method it is frequently difficult to guarantee reproducible conditions, which frequently entails fluctuations in quality. Methods for producing stabilized surfactant agents having a pearlescent effect should therefore have as few steps as possible with strong heat input.

Use of hydrogenated castor oils for stabilizing insoluble constituents in surfactant agents, wherein the hydrogenated castor oils are incorporated into the surfactant agent in a hot process is known (DE 102006032505, EP 2037877 B1). If the methods described here are applied, it entails previously described disadvantage of an additional production step using heat.

A cold process for provision of pearlescent waxes in aqueous surfactant solutions is known from DE 19921187 A1 (EP1177274 B1). However, the method requires simultaneous addition of pearlescent waxes in combination with polyolesters, which lower the melting point of the pearlescent waxes.

The subject of the present disclosure was to provide a composition for stabilization of pearlescent agents, such as shampoos or shower gels, wherein said composition can be mixed cold with the agent containing pearlescent substances. It was also a subject of the present disclosure to provide a simple method for stabilization of agents containing pearlescent substances, wherein an additional heat application is not necessary.

BRIEF SUMMARY

Aqueous dispersions and methods including aqueous dispersions are provided herein. In an exemplary embodiment, an aqueous dispersion of hydrogenated castor oil for stabilization of aqueous surfactant agents comprising pearlescent waxes and/or pearlescent pigments, which, relative to the total weight of the aqueous dispersion, comprises:
(a) from about 1 to about 25 wt. % hydrogenated castor oil,
(b) from about 2 to about 30 wt. % of one or more anionic surfactants,
(c) from about 2 to about 30 wt. % of one or more amphoteric surfactants, and
(d) from about 2 to about 30 wt. % of one or more nonionic surfactants.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has surprisingly been found that this can be achieved with an aqueous composition containing hydrogenated castor oil and a combination of anionic, nonionic and amphoteric surfactants. With the use of surfactants in specific quantities in this composition, the hydrogenated castor oil is distributed very finely. Surprisingly, a clear stabilization of surfactant agents containing pearlescent substances was observed when the stabilizing mixture as contemplated herein was incorporated in a cold state into a surfactant agent containing pearlescent substances.

The present disclosure relates to:
1. An aqueous dispersion of hydrogenated castor oil for stabilization of aqueous surfactant agents containing pearlescent waxes and/or pearlescent pigments, which, relative to its total weight, contains:
(a) from about 1 to about 25 wt. % hydrogenated castor oil,
(b) from about 2 to about 30 wt. % of one or more anionic surfactants,
(c) from about 2 to about 30 wt. % of one or more amphoteric surfactants, and
(d) from about 2 to about 30 wt. % of one or more nonionic surfactants.
2. A dispersion according to point 1 above, containing the following relative to its total weight:
(a) from about 2.5 to about 15 wt. % hydrogenated castor oil,
(b) from about 2.5 to about 10 wt. % of one or more anionic surfactants,
(c) from about 5 to about 15 wt. % of one or more amphoteric surfactants, and (d) from about 5 to about 15 wt. % of one or more nonionic surfactants.

3. A dispersion according to point 1 or 2 above, wherein the dispersion does not contain a cationic surfactant.

4. A dispersion according to point 1 or 2 above, wherein the dispersion does not contain polyolester.

5. A dispersion according to one of the points above, wherein an alkali or ammonium salt of lauryl ether sulfate with a degree of ethoxylation of from 2 to 4 ethylene oxide groups or a mixture thereof is contained.

6. A dispersion according to one of the points above, wherein one or more betaines are contained as the amphoteric surfactant (c), preferably cocamidopropyl hydroxysultains (INCI) and/or cocamidopropyl betaine (INCI).

7. A dispersion according to one of the points above, wherein the nonionic surfactant (d) is selected from
ethylene oxide addition products on saturated linear fatty alcohols and/or fatty acids each having from 2 to 30 moles of ethylene oxide per mole of fatty alcohol and/or fatty acid,
$C_{12}$-$C_{30}$ fatty acid ester of addition products of from 1 to 30 moles of ethylene oxide on glycerin,
addition products of from 5 to 60 moles of ethylene oxide on hardened castor oil and
mixtures thereof.

8. A dispersion according to one of the points above, wherein the nonionic surfactant is selected from
ethylene oxide addition products on saturated linear fatty alcohols and/or fatty acids each having from 2 to 30 moles of ethylene oxide per mole of fatty alcohol and/or fatty acid, an/or
$C_{12}$-$C_{30}$ fatty acid ester of addition products of from 1 to 30 moles of ethylene oxide on glycerin, and/or
addition products of from 5 to 60 moles of ethylene oxide on hardened castor oil.

9. A dispersion according to one of the points above, wherein the nonionic surfactant (d) is selected from, laureth-4 (INCI), PEG-7 glycerol cocoate (INCI), PEG-40 hydrogenated castor oil (INCI) and mixtures thereof.

10. A dispersion according to one of the points above, wherein the dispersion has a pH value in the range of from about 4.5 to about 5.5.

11. A dispersion according to one of the points above, wherein the dispersion contains from about 40 to about 90 wt. %, preferably from about 50 to about 85 wt. % and particularly from about 60 to about 80 wt. % water relative to its total weight.

12. A dispersion according to one of the points above, wherein the dispersion contains only water as a carrier.

13. A method for production of a stabilized surfactant-containing aqueous agent having a pearlescent effect, wherein a dispersion according to one of points 1 to 12 above is introduced to an aqueous agent containing pearlescent wax and/or pearlescent pigments in a cold process.

14. A method for producing a stabilized surfactant-containing aqueous agent having a pearlescent effect, wherein a dispersion according to one of points 1 to 12 above is introduced to a surfactant-containing aqueous agent containing anti-dandruff pigments, preferably zinc pyrithion, in a cold process.

15. A method according to point 13 or 14 above, wherein the surfactant-containing aqueous agent is a cosmetic cleaning agent, particularly a shampoo or shower gel.

16. A method according to point 13 or 14 above, wherein the surfactant-containing aqueous agent contains one or multiple components from the group of titanium dioxide, iron oxide and mice.

17. A method according to one of points 13 to 16 above, wherein the quantity of hydrogenated castor oil introduced in a stabilized surfactant-containing aqueous agent is from about 0.1 to about 1 wt. %, preferably from about 0.2 to about 0.5 wt. %.

18. Use of a dispersion according to one of points 1 to 12 above for stabilization of surfactant-containing aqueous agents, particularly shampoos or shower gels containing pearlescent waxes and/or pearlescent pigments.

19. Use of a dispersion according to one of points 1 to 12 above for stabilization of surfactant-containing aqueous agents, particularly shampoos or shower gels containing anti-dandruff pigments, particularly zinc pyrithion.

20. Use according to one of claim 18 or 19, wherein the proportion by weight of the dispersion according to one of points 1 or 12 of the total weight of the surfactant-containing aqueous agent is from about 0.5 to about 10 wt. %, preferably from about 1 to about 8 wt. % and particularly from about 1.5 to about 6 wt. %.

The stabilization mixture as contemplated herein is a dispersion of hydrogenated castor oil in an aqueous phase. With the surfactants used and adherence to the specified quantities,
the hydrogenate castor oil is distributed very finely in the aqueous phase. The dispersion as contemplated herein is often referred to hereinafter simply as a stabilization mixture.

Surprisingly, if the stabilization mixture as contemplated herein is mixed cold with an aqueous surfactant agent containing pearlescent substances, such as pearlescent waxes and/or pearlescent pigments, a clear stabilization of the pearlescent substances in the surfactant agent is achieved. Stabilization as contemplated herein is understood to means that essentially no phase separations occur in the obtained surfactant agent in conventional storage stability tests, for example at a temperature of from about 40 to about 50° C., and no visible changes appear over extended periods at room temperature.

Aqueous surfactant agents that can be stabilized by the stabilization mixture as contemplated herein are understood to means, in particular, surfactant cleaning agents having pearlescence, preferably cosmetic cleaning agents such as shampoos or shower gels, as well as dishwashing agents.

An essential component of the stabilization mixture as contemplated herein is hydrogenated castor oil. Hydrogenated castor oil is sold, for example, under the name Cutina® HR (BASF). Hydrogenated castor oils that can be used in the present disclosure normally have a melting point in the range of from about 60 to about 100° C., preferably from about 70 to about 90° C., more preferably from about 80 to about 90° C., particularly from about 85 to about 88° C.

As contemplated herein, polyalkoxylated or polyethoxylated derivatives or addition products of hydrogenated castor oil are not encompassed by the term "hydrogenated castor oil".

The hydrogenated castor oil is contained in the stabilization mixture as contemplated herein in a quantity of from about 1 to about 25 wt. %, preferably from about 2.5 to about 15 wt. %, more preferably from about 5 to about 10 wt. %, relative to the total weight of the stabilization mixture in each case.

Furthermore, the stabilization mixture as contemplated herein contains anionic, amphoteric and nonionic surfactants as necessary components. The surfactants should be suitable for contact with the human body, particularly if they are used in end products for care and/or cleaning of the human body.

As contemplated herein, the following anionic surfactant substances are suitable as anionic surfactants. They are exemplified by a water-solubilizing anionic group, such as a carboxylate, sulfate or sulfate group, sulfonate or phosphate group and a lipophilic alkyl group having about from 8 to 30 carbon atoms. Furthermore, the molecule can contain glycol or polyglycol ether groups, ester, ether and amide groups, as well as hydroxyl groups. Examples of suitable anionic surfactants are, each in the form of sodium, potassium and ammonium salts, as well as mono-, di- and trialkanol ammonium salts having from 2 to 4 carbon atoms in the alkanol group, linear and branched fatty acids having from about 8 to about 30 carbon atoms (soap), ether carboxylic acids having the formula R—O—$(CH_2—CH_2O)_x$—$CH_2$—COOH, wherein R is a linear alkyl group having from 8 to 30 carbon atoms and x=0 or from 1 to 16, acyl sarcosides having from 8 to 24 carbon atoms in the acyl group, acyl tauride having from 8 to 24 carbon atoms in the acyl group, acyl isethionates having from 8 to 24 carbon atoms in the acyl group, sulfosuccinic acid mono- and dialkyl esters having from 8 to 24 carbon atoms in the alkyl group and sulfusuccinic acid monoalkyl polyoxyethyl esters having from 8 to 24 carbon atoms in the alkyl group and from 1 to 6 oxyethyl groups, linear alkane sulfonates having from 8 to 24 carbon atoms, linear alpha olefin sulfonates having from 8 to 24 carbon atoms, alpha sulfo-fatty acid methyl esters of fatty acids having from 8 to 30 carbon atoms, alkyl sulfates and alkyl polyglycol ether sulfates having the formula R—$O(CH_2—CH_2O)_x$—$OSO_3H$, wherein R is a preferred linear alkyl group having from 8 to 30 carbon atoms and x=0 or from 1 to 12, mixtures of surfactant hydroxysulfonates according to DE-A-37 25 030, sulfated hydroxyalkyl polyethylene and/or hydroxyalkyl propylene glycol ethers according to DE-A-37 23 354, sulfonates of unsaturated fatty acids having from 8 to 24 carbon atoms and from 1 to 6 double bonds according to DE-A-39 26 344, esters of tartaric acid and citric acid having alcohols, which are the addition products of about from 2-15 molecules of ethyl oxide and/or propylene oxide on fatty alcohols having from 8 to 22 carbon atoms, alkyl- and/or alkenyl ether phosphates of formula (II),

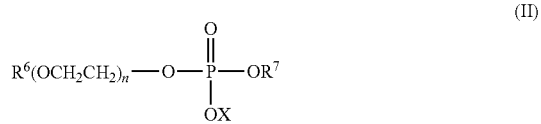

(II)

wherein $R^6$ preferably denotes an aliphatic hydrocarbon radical having from 8 to 30 carbon atoms, $R^7$ for hydrogen, a radical $(CH_2CH_2O)_nR^6$ or X, n denotes numbers from 1 to 10 and X denotes hydrogen, an alkali or alkaline earth metal or $NR^8R^9R^{10}R^{11}$, with $R^8$ to $R^{11}$ denoting a $C_1$ to $C_4$ hydrocarbon radical independently of each other, sulfated fatty acid alkylene glycol esters of formula (III), $R^{12}CO(AlkO)_nSO_3M$ (III)

in $R^{12}CO$ denotes a linear or branched, aliphatic, saturated and/or unsaturated acyl radical having from 6 to 22 carbon atoms, alcohol denotes $CH_2CH_2$, $CHCH3CH2$ and/or $CH_2CHCH_3$, n denotes numbers from 0.5 to 5 and M denotes a cation, as described in DE-OS 197 36 906.5, monoglyceride sulfates and monoglyceride ether sulfates of formula (IV), as described, for example, in EP-B1 0 561 825, EP-B1 0 561 999, DE-A1 42 04 700 or by A. K. Biswas et al. in J. Am. Oil. Chem. Soc. 37, 171 (1960) and F. U. Ahmed in J. Am. Oil. Chem. Soc. 67, 8 (1990),

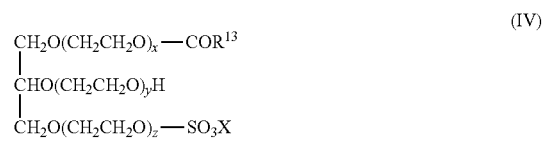

(IV)

wherein $R^{13}CO$ denotes a linear or branched acyl radical having from 6 to 22 carbon atoms, x, y and z in total denote 0 or numbers from 1 to 30, preferably from 2 to 10, and X denotes an alkali or alkaline earth metal. Typical examples of monoglyceride (ether) sulfates suitable for the purposes of the present disclosure are the reaction products of lauric acid monoglyceride, coconut fatty acid monoglyceride, palmitic acid monoglyceride, stearic acid monoglyceride, oleic acid monoglyceride and tallow fatty acid monoglyceride, and also the ethylene oxide adducts thereof sulfur trioxide or chlorosulfonic acid in the form of their sodium salts. Preferably, monoglyceride sulfates of formula (IV) are used, wherein $R^{13}CO$ denotes a linear acyl radical having from 8 to 18 carbon atoms.

Preferred surfactants are alkyl sulfates, alkyl polyglykol ether sulfates and ether carboxylic acid salts having from 10 to 18 carbon atoms in the alkyl group and up to 12 glycol ether groups in molecules of sulfosuccinic acid mono- and dialkyl esters having from 8 to 18 carbon atoms in the alkyl group and sulfusuccinic acid monoalkyl polyoxyethyl esters having from 8 to 18 carbon atoms in the alkyl group and from 1 to 6 oxyethyl groups.

Particularly preferred anionic surfactants are the alkali metal or ammonium salts of lauryl ether sulfate having a degree of ethoxylation of from 2 to 4 EO, such as the commercially available anionic surfactant with the INCI name sodium laureth sulfate.

The anionic surfactant is contained in the stabilization mixture as contemplated herein in a quantity of from about 2 to about 30 wt. %, preferably from about 2 to about 10 wt. %, more preferably from about 2.5 to about 5 wt. % relative to the total weight of the stabilization mixture.

Amphoteric or zwitterionic surfactants are surface active compounds, which have at least one quarternary ammonium group and at least one —$COO^{(-)}$— or —$SO_3^{(-)}$ group in the molecule. Particularly suitable amphoteric surfactants are the so-called betaines such as the n-alkyl-n, n-dimethylammonium glycinates, for example coco-alkyldimethyl ammonium glycinate, n-acylaminopropyl-n, n-dimethyl ammonium glycinates, for example coco-acylaminopropyldimethyl ammonium glycinate, and 2-alkyl-3-carboxymethyl-3-hydroxyethyl imidazolines each having from 8 to 18 carbon atoms in the alkyl or acyl group and coco-acylaminoethylhydroxyethyl carboxymethyl glycinate, as well as sultaines or sulfobetaines. Particularly preferred amphoteric surfactants include the compounds known by the INCI names cocamidopropyl betaine and cocamidopropyl hydroxysultaine.

As contemplated herein, amphoteric surfactants are also understood to mean surfactant compounds which, apart from a $C_8$-$C_{24}$ alkyl or acyl group, contain at least one free amino group and at least one COOH or —$SO_3H$ group in the molecule and are capable of forming internal
salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 24 carbon atoms in the alkyl group. Preferred amphoteric surfactants include n-coco-alkylaminopropionate, coco-acylaminoethylaminopropionate and $c_{12}$-$c_{18}$ acylsarcosine.

The amphoteric surfactant is contained in the stabilization mixture as contemplated herein in a quantity of from about 2 to about 30 wt. %, preferably from about 2 to about 20 wt. %, more preferably from about 5 to about 15 wt. % relative to the total weight of the stabilization mixture.

Nonionic surfactants include, for example, at least one polyol group, a polyalkylene glycole ether group or a combination of a polyol and polyglycol ether group. Examples of such compounds include addition products of from 2 to 50 moles of ethylene oxide and/or from 0 to 5 moles of propylene oxide on linear and branched fatty alcohols having from 8 to 30 carbon atoms on fatty acids having from 8 to 30 carbon atoms and on alkylphenols having from 8 to 15 carbon atoms in the alkyl group, with a methyl or $C_2$-$C_6$-alkyl radical end group-closed addition products of from 2 to 50 moles of ehtylene oxide and/or from 0 to 5 moles of propylene oxide on linear and branched fatty alcohols having from 8 to 30 carbon atoms on fatty acids having from 8 to 30 carbon atoms and on alkyl phenols having from 8 to 15 carbon atoms in the alkyl group, such as the types available under the trade names Dehydol® LS (BASF) and Dehydol® LT (BASF).

$C_{12}$-$C_{30}$ fatty acid mono- and diesters of addition products of from 1 to 30 moles of ethylene oxide on glycerin, addition products of from 5 to 60 moles of ethylene oxide on castor oil and hardened castor oil, such as castor-oil-hydrogenated+40 EO, such as the product available under the trade name Cremophor CO 455 (BASF) (INCI: PEG-40 Hydrogenated Castor Oil), polyol fatty acid esters, such as the commercial product Hydagen® HSP (BASF) or Sovermol types (BASF), alkoxylated triglycerides, alkoxylated fatty acid alkyl esters of formula (V)

$$R^{14}CO\text{—}(OCH_2CHR^{15})_w OR^{16} \quad (V)$$

wherein $R^{14}$ denotes a linear branched, saturated and/or unsaturated acyl radical having from 6 to 22 carbon atoms, $R^{15}$ denotes hydrogen or methyl, $R^{16}$ denotes linear or branched alkyl radicals having from 1 to 4 carbon atoms and w denotes numbers from 1 to 20, amonoxides, hydroxy mixed ethers, as described in DE-OS 197 38 866, sorbitan fatty acid esters and addition products of ethylene oxide onto sorbitan fatty acid esters such as polysorbates, sugar fatty acid esters and addition products of ethylene oxide on sugar fatty acid esters, addition products of ethylene oxide on fatty acid alkanolamides and fatty amines, fatty-acid-n-aklylglucamides, alkyl polyglycosides corresponding to the general formula RO—(Z)x, wherein R denotes alkyl, Z denotes sugar and x denotes the number of sugar units. The alkyl polyglycosides can only contain a certain alkyl radical R. However, these compounds are normally produced from natural fats and oils. In this case, mixtures corresponding to the initial compounds and/or the the corresponding reworking of these compounds as alkyl radicals R.

In preferred alkyl polyglycosides, R consists
essentially of $C_8$- and $C_{10}$-alkyl groups,
essentially of $C_{12}$- and $C_{14}$-alkyl groups,
essentially of $C_8$- to $C_{16}$-alkyl groups or
essentially of $C_{12}$- to $C_{16}$-alkyl groups or
essentially of $C_{16}$- to $C_{18}$-alkyl groups.

Any arbitrary mono- or oligosaccharide can be used as sugar component Z. Normally, sugars having about 5 or about 6 carbon atoms and the corresponding oligosaccharides are used. Examples of such sugars are glucose, fructose, galactose, arabinose, ribose, xylose, allose, altrose, mannose, gulose, idose, talose and sucrose. Preferred sugar components are glucose, fructose, galactose, arabinose and sucrose; glucose is particularly preferred.

The alkyl polyglycosides used as contemplated herein contain an average of from about 1.1 to about 5 sugar units. Alkyl polyglycosides having x-values from about 1.1 to about 2.0 are preferred. Alkyl polyglycosides in which x is from about 1.1 to about 1.8 are more preferable.

The alkyloxylated homologs of said alkyl polyglycosides can be used as contemplated herein. These homologs can contain an average of up to about 10 ethylene oxide and/or propylene oxide units per alkyl glycoside unit.

Preferred non-ionic surfactants have been found to be alkylene oxide addition products on saturated fatty alcohols and fatty acids having from 2 to 30 moles of ethylene oxide per mole of fatty alcohol or fatty acid. Preparations with outstanding properties are also obtained if they contain fatty acid esters of ethoxylated glycerol as nonionic surfactants.

These compounds are exemplified by the following parameters. The alkyl radical R contains from 6 to 22 carbon atoms and can be linear or branched. Preference is given to primary linear aliphatic radicals and aliphatic radicals which are methyl-branched in the 2-position. Examples of said alkyl radicals are 1-Octyl, 1-Decyl, 1-Lauryl, 1-Myristyl, 1-Cetyl and 1-Stearyl. 1-Octyl, 1-Decyl, 1-Lauryl, 1-Myristyl are particularly preferred. With use of so-called "oxo-alcohols" as starting materials, compounds having an odd number of carbon atoms in the alkyl chain predominate.

The compounds having alkyl groups used as surfactant can be uniform substances in each case. It is normally preferable if the production of these substances starts with plant- or animal-based raw materials so that substance mixtures having different alkyl chain lengths depending on the raw material are obtained.

Examples of preferred ethoxylated fatty alcohols having an average degree of ethoxylation of 2 to 29 are Laureth-2, Oleth-2, Ceteareth-2, Laneth-2, Laureth-3, Oleth-3, Ceteareth-3, Laureth-4, Oleth-4, Ceteareth-4, Laneth-4, Laureth-5, Oleth-5, Ceteareth-5, Laneth-5, Deceth-7, Laureth-7, Oleth-7, Coceth-7, Ceteth-7, Ceteareth-7, C11-15 Pareth-7, Laureth-9, Oleth-9, Ceteareth-9, Laureth-10, Oleth-10, Beheneth-10, Ceteareth-10, Laureth-12, Ceteareth-12, Trideceth-12, Ceteth-15, Laneth-15, Ceteareth-15, Laneth-16, Ceteth-16, Oleth-16, Steareth-16, Oleth-20, Ceteth-20, Ceteareth-20, Laneth-20, Steareth-21, Ceteareth-23, Ceteareth-25, Ceteareth-27. Use of a mixture of Steareth-2 and Steareth-21 is particularly preferred.

Furthermore, preference is given to mono-, di- and tricarboxylic acid esters of saturated and/or unsaturated linear and/or branched carboxylic acids with glycerin, which can have from 1 to 10, particularly from 7 to 9 ethylene oxide units, such as PEG-7 glyceryl cocoate.

Additional preferred nonionic surfactants are the PEG derivatives of hydrogenated castor oil, such as the products available under the name PEG Hydrogenated Castor Oil, including PEG-30 Hydrogenated Castor Oil, PEG-33 Hydrogenated Castor Oil, PEG-35 Hydrogenated Castor Oil, PEG-36 Hydrogenated Castor Oil and PEG-40 Hydrogenated Castor Oil. As contemplated herein, preference is given to the use of PEG-40 Hydrogenated Castor Oil.

Among the aforementioned nonionic surfactants, compounds having the INCI names Laureth-4 (INCI), PEG-7 Glycerol Cocoate (INCI), PEG-40 Hydrogenated Castor Oil (INCI) and mixtures thereof are particularly preferred.

The nonionic surfactant is contained in the stabilization mixture as contemplated herein in a quantity of from about 2 to about 30 wt. %, preferably from about 2 to about 20 wt. %, more preferably from about 5 to about 15 wt. % relative to the total weight of the stabilization mixture.

The stabilization mixture as contemplated herein can also contain a cationic surfactant. The stabilization mixture as contemplated herein preferably does not include a cationic surfactant. Examples of cationic surfactants are quaternary ammonium compounds, esterquats or amidoamines.

The total quantity of surfactants is preferably contained in the stabilization mixture as contemplated herein in a quantity of from about 10 to about 40 wt. %, preferably from about 12.5 to about 35 wt. %, more preferably from about 15 to about 30 wt. %, relative to the total weight of the stabilization mixture in each case.

The stabilization mixture as contemplated herein is an aqueous dispersion and, therefore, contains water as a carrier. Preference is given to dispersions containing from about 40 to about 90 wt. %, preferably from about 50 to about 85 wt. % and particularly from about 60 to about 80 wt. % water, relative to the total weight. It is also preferred that no carrier other than water is included.

The stabilization mixture as contemplated herein is normally acidic and can contain conventional pH regulators, such as citric acid. The pH value of the stabilization mixture as contemplated herein is preferably in a range of from about 4 to about 6, more preferably from about 4.5 to about 5.5.

The stabilization mixture as contemplated herein contains, in addition to the aforementioned surfactants, water and the optional pH regulator, less than about 10 wt. %, preferably less than about 5 wt. % and particularly less than about 2 wt. % of additional components.

Therefore, an additional preferred subject of the present application is an aqueous dispersion of hydrogenated castor oil for stabilization of aqueous surfactant agents containing pearlescent waxes and/or pearlescent pigments, which, relative to its total weight, contains:
(a) from about 1 to about 25 wt. % hydrogenated castor oil,
(b) from about 2 to about 30 wt. % of one or more anionic surfactants,
(c) from about 2 to about 30 wt. % of one or more amphoteric surfactants, and
(d) from about 2 to about 30 wt. % of one or multiple nonionic surfactants
(e) from about 40 to about 90 wt. % water
and less than about 10 wt. %, preferably less than about 5 wt. % and particularly less than about 2 wt. % of additional components.

An especially preferred subject of the present application is an aqueous dispersion of hydrogenated castor oil for stabilization of aqueous surfactant agents containing pearlescent waxes and/or pearlescent pigments, which, relative to its total weight, contains:
(a) from about 2.5 to about 15 wt. % hydrogenated castor oil,
(b) from about 2.5 to about 10 wt. % of one or more anionic surfactants,
(c) from about 5 to about 15 wt. % of one or more amphoteric surfactants, and
(d) from about 5 to about 15 wt. % of one or multiple nonionic surfactants
(e) from about 60 to about 80 wt. % water
and less than about 10 wt. %, preferably less than about 5 wt. % and particularly less than about 2 wt. % of additional components.

The viscosity of the stabilization mixture as contemplated herein is about 10,000 mPas or less (Brookfield viscosimeter, 20° C., 60 s, spindle 5, 20 UpM).

The stabilization mixture as contemplated herein can also contain conventional additives, such as preservatives, perfumes, etc. Preferred embodiments are such that contain components in addition to hydrogenated castor oil, water, anionic surfactants, nonionic surfactants and amphoteric surfactants, a pH regulator, if applicable and a preservative, if applicable.

The stabilization mixture as contemplated herein can be produced according to known methods. For example a first mixture of one part water, anionic and amphoteric surfactants and, if applicable a weak acid for pH adjustment and a preservative can be prepared and heated. Then a second mixture of hydrogenated castor oil and the nonionic surfactant, which was first melted at a temperature of from about 90 to about 100° C., for instance, can be added to the first mixture and homogenized at from about 80 to about 90° C. Finally, the remaining part of the water is added in an unheated state and the mixture is cooled while being stirred and homogenizing.

If the mixture is to be used in the same way for producing a stabilized surfactant-containing aqueous agent having a pearlescent effect, it is sufficient to carry out the cooling down to a temperature of approximately 30 to 40° C.

The present disclosure also relates to a method for producing a surfactant-containing aqueous agent having a pearlescent effect, wherein a stabilization mixture as contemplated herein is added to a surfactant-containing aqueous agent having pearlescent waxes and/or pearlescent pigments in a cold process. As contemplated herein, the surfactant-containing aqueous agent is preferably a cosmetic cleaning agent, particularly a shampoo or shower gen, but can also be a non-cosmetic cleaning agent, such as a dishwashing agent.

As contemplated herein, pearlescent waxes and/or pearlescent pigments are preferred pearlescent substances. Pearlescent waxes and pearlescent pigments are known as such. Examples of pearlescent waxes include: alkylene glycol esters, fatty acid alkanolamides, partial glycerides, esters of polyhydric, possibly hydroxy-substituted carboxylic acids, fatty alcohols, fatty acids, fatty ketones, fatty aldehydes, fatty ethers, fatty carbonates, ring-opening products of olefin epoxides and mixtures thereof.

As contemplated herein, however, the usable pearlescent waxes do not include hydrogenated castor oil as a component (a) of the stabilization mixture as contemplated herein. Pearlescent pigments are usually platelet-shaped pigments which achieve a luster effect by employing light reflection. Preferred examples are mica, titanium dioxide, iron oxide, such as $Fe_2O_3$ and $Fe_3O_4$, and combinations thereof.

Surprisingly, it has been found, that the inventive method is also suitable for producing a stabilized surfactant-containing aqueous agent having an anti-dandruff effect, wherein a stabilization mixture as contemplated herein is added to a surfactant-containing aqueous agent containing anti-dandruff pigments, preferably zinc pyrithion, in a cold process.

A particular advantage of the stabilization mixture as contemplated herein is its suitability to be mixed with surfactant-containing aqueous agent in a cold process, by employing which a stabilized pearlescent agent is obtained. This means, in particular, that the contained pearlescent substance does not aggregate and/or separate in normal storage conditions, so no visible change or phase separation occurs. Therefore, an extremely simple method is provided for production of a stable surfactant pearlescent agent by employing the present disclosure. As a result, disadvantages of an additional heating step and resulting quality fluctuations and reductions are avoided.

As contemplated herein "cold process" should be understood to mean that mixture with the surfactant pearlescent agent is normally carried out at a temperature of the stabilization mixture of from about 15 to about 35° C. This also includes temperatures slightly above room temperature, which simplifies the processing of the mixture (i.e. pumping and dispensing compatibility). It is surprising that an even higher temperature is not necessary, for example, to melt the dispersed hydrogenated castor oil first.

In the production of a surfactant-containing aqueous agent having a pearlescent effect as contemplated herein, the mixture ratio of the dispersion to the cleaning agent is preferably from about 1:5 to about 1:20, more preferably from about 1:5 to about 1:10, particularly about 1:9. In general, the mixture ratio can be selected so that an end concentration of hydrogenated castor oil in the produced surfactant-containing aqueous agent of approximately from about 0.1 to about 1 wt. % is obtained, preferably from about 0.2 to about 0.5 wt. %. If applicable, the stabilization mixture must first be diluted with water beforehand.

If the dispersion as contemplated herein and/or stabilization mixture for stabilization of surfactant-containing aqueous agents is diluted with water before mixture with the cleaning agent, the mixture ratio of the dispersion as contemplated herein is preferably from about 1:9 to about 1:1, more preferably from about 1:5 to about 1:1.

After dilution, the aqueous dispersion of hydrogenated castor oil for stabilization of aqueous surfactant agents containing pearlescent waxes and/or pearlescent pigments, which, relative to its total weight, preferably contains:
(a) from about 1 to about 15 wt. % hydrogenated castor oil,
(b) from about 0.2 to about 10 wt. % of one or more anionic surfactants,
(c) from about 1 to about 12 wt. % of one or more amphoteric surfactants, and
(d) from about 1 to about 12 wt. % of one or multiple nonionic surfactants
(e) from about 70 to about 96 wt. % water.

The present disclosure also relates to the use of the dispersion as contemplated herein and/or stabilization mixture for stabilization of surfactant-containing aqueous agents, particularly shampoos or shower gels containing pearlescent waxes and/or pearlescent pigments.

Furthermore, the present disclosure relates to the use of the dispersion as contemplated herein and/or stabilization mixture for stabilization of surfactant-containing aqueous agents, particularly shampoos or shower gels containing anti-dandruff pigments, particularly zinc pyrithion.

In the preferred embodiment of the inventive uses, the proportion by weight of the dispersion as contemplated herein and/or stabilization mixture for stabilization of surfactant-containing aqueous agents is from about 0.5 to about 10 wt. %, preferably from about 1 to about 8 wt. % and particularly from about 1.5 to about 6 wt. %.

Overview Table:

The preferred stabilization mixtures as contemplated herein are listed below. Formulations are in wt. % and relate to the active ingredient concentration.

|  | Formula 1 | Formula 2 | Formula 3 | Formula 4 |
|---|---|---|---|---|
| Hydrogenated Castor Oil | 1 to 25 | 2 to 20 | 2.5 to 15 | 5 to 10 |
| Anionic surfactant(s) | 2 to 30 | 2 to 15 | 2 to 10 | 2.5 to 5 |
| Amphoteric surfactant(s) | 2 to 30 | 3 to 20 | 5 to 15 | 5 to 15 |
| Nonionic surfactant(s) | 2 to 30 | 3 to 20 | 5 to | 5 to 15 |
| Misc | add 100 | add 100 | add 100 | add 100 |

|  | Formula 1a | Formula 2a | Formula 3a | Formula 4a |
|---|---|---|---|---|
| Hydrogenated Castor Oil, melting point 85-88° C. | 1 to 25 | 2 to 20 | 2.5 to 15 | 5 to 10 |
| Anionic surfactant(s): $C_{10}$-$C_{18}$ alkyl ether sulfate | 2 to 30 | 2 to 15 | 2 to 10 | 2.5 to 5 |
| Amphoteric surfactant(s): Betaine(s) and/or sultain(s) | 2 to 30 | 3 to 20 | 5 to 15 | 5 to 15 |
| Nonionic surfactant(s): Ethylene oxide addition products on saturated linear fatty alcohols and/or fatty acids each having 2 to 30 moles of ethylene oxide per mole of fatty alcohol and/or fatty acid, an/or $C_{12}$-$C_{30}$ fatty acid ester of addition products of 1 to 30 moles of ethylene oxide on glycerin, and/or Addition products of 5 to 60 moles of ethylene oxide on hardened castor oil | 2 to 30 | 3 to 20 | 5 to | 5 to 15 |

-continued

| pH | 4 to 6 | 4 to 6 | 4 to 6 | 4 to 6 |
|---|---|---|---|---|
| Misc | add 100 | add 100 | add 100 | add 100 |

| | Formula 1b | Formula 2b | Formula 3b | Formula 4b |
|---|---|---|---|---|
| Hydrogenated Castor Oil, melting point 85-88° C. | 1 to 25 | 2 to 20 | 2.5 to 15 | 5 to 10 |
| Anionic surfactant(s): Alkali or ammonium salt of lauryl ether sulfate having a degree of ethoxylation of 2 to 4 ethylene oxide groups | 2 to 30 | 2 to 15 | 2 to 10 | 2.5 to 5 |
| Amphoteric surfactant(s): Cocamidopropyl hydroxysultaine (INCI) and/oder cocamidopropyl betaine (INCI) | 2 to 30 | 3 to 20 | 5 to 15 | 5 to 15 |
| Nonionic surfactant(s): Laureth-4 (INCI), PEG-7 glycerol cocoate (INCI) and/or PEG-40 Hydrogenated Castor Oil (INCI) | 2 to 30 | 3 to 20 | 5 to | 5 to 15 |
| pH | 4 to 6 | 4 to 6 | 4 to 6 | 4 to 6 |
| Misc | add 100 | add 100 | add 100 | add 100 |

As contemplated herein "Misc" should be understood to mean essentially water. Optionally,
an acid for pH adjustment or a preservative can be included. Preferably, no cationic surfactants are included under "Misc".

EXAMPLES

1. Stabilization Mixtures

Production took place in the aqueous dispersions of hardened castor oil listed in Table 1 below. The quantity formulations indicate percent by weight, unless otherwise specified.

The production took place by preparing a first mixture from half of the water used, the anionic and amphoteric surfactant, citric acid and sodium benzoate, dissolving the mixture and heating it to about 80° C. Then a second mixture of hydrogenated castor oil and the nonionic surfactant, which was first melted at a temperature of from about 90-about 100° C., for instance, was added to the first mixture, mixed at a temperature from about 80 to about 90° C. and homogenized under heat for about 15 minutes. Then the remaining part of the water was added in an unheated state and the mixture was cooled to about 35° C. and homogenized while stirring in a vacuum.

The pH value of the produced stabilization mixture was in the range of from about 4.5 to about 5.5. The viscosity was less than about 10,000 mPas (Brookfield viscosimeter, 20° C., 60 s, spindle 5, 20 UpM).

TABLE 1

| INCI or other name | Surfactant type | Example 1 | Example 2 | Example 3 | Example 4 | Example 5 |
|---|---|---|---|---|---|---|
| Water | — | 44.25 | 41.75 | 39.25 | 51.80 | 46.75 |
| Sodium Benzoate | — | 0.50 | 0.50 | 0.50 | 0.50 | 0.50 |
| Citric Acid | — | 0.25 | 0.25 | 0.25 | 0.25 | 0.25 |
| Cocamidopropyl Hydroxysultaine 50% | Amphoter | 25.00 | 30.00 | — | — | — |
| Cocamidopropyl Betaine 40% | Amphoter | — | — | 30.00 | 15.00 | 30.00 |
| Sodium Laureth Sulfate 25% | Anionic | 15.00 | 10.00 | 10.00 | 15.00 | 10.00 |
| Hydrogenated Castor Oil, melting point 85-88° C. | — | 5.00 | 10.00 | 5.00 | 10.00 | 5.00 |
| Laureth-4 | Nonionic | — | 7.50 | — | — | 7.50 |
| PEG-40 Hydrogenated Castor Oil | Nonionic | — | — | — | 7.50 | — |
| PEG-7 Glyceryl Cocoate | Nonionic | 10.00 | — | 15.00 | — | — |
| | | 100.00 | 100.00 | 100.00 | 100.00 | 100.00 |

The appearance of the stabilization mixtures in examples 1 to 5 was homogeneously milky.

2. Production of Stabilized Pearlescent Shampoos

The stabilization mixtures that were obtained in examples 1 to 5, having a temperature of about 35° C., were mixed with a base shampoo specified in Table 2 below having ambient temperature while stirring. The stabilizing mixtures were first diluted in the ratios specified in Table to for the mixing process.

For the purpose of comparison, the base shampoo was mixed with a corresponding amount of water and by directly introducing hydrogenated castor oil in a hot process. The mixture ratio of stabilization mixture and/or comparison mixture to base shampoo was about 1:9 in each case.

The pH value of the produced stabilization mixture was in the range of from about 4.5 to about 5.5. The viscosity was from about 7000 to about 10,000 mPas (Brookfield viscosimeter, 20° C., 60 s, spindle 5, 20 UpM).

The stabilities of the obtained stabilized shampoos were visually evaluated after about 5 days of storage at about 45° C. and about 50° C. The results are presented in Table 3.

TABLE 3

Stability tests

| | Storage temperature | Evaluation |
|---|---|---|
| No stabilization (water added) | 45° C. | Complete separation |
| | 50° C. | Complete separation |
| Stabilization with hydrogenated castor oil (hot process) | 45° C. | Clear separation |
| | 50° C. | Clear separation |
| Stabilization with Ex. 1 | 45° C. | No change |
| | 50° C. | Slight separation |

TABLE 2

Base shampoo and mixture with stabilization mixtures

| INCI or other name Base shampoo | No stabiliz. (water added) | Stabiliz. with hydrog. castor oil (hot process) | Stab. with Ex. 1 | Stab. with Ex. 2 | Stab. with Ex. 3 | Stab. with Ex. 4 | Stab. with Ex. 5 |
|---|---|---|---|---|---|---|---|
| Sodium Laureth Sulfate 70% | 14.50 | 14.50 | 14.50 | 14.50 | 14.50 | 14.50 | 14.50 |
| Water | 53.65 | 53.65 | 53.65 | 53.65 | 53.65 | 53.65 | 53.65 |
| Disodium Cocoamphodiacetate | 8.00 | 8.00 | 8.00 | 8.00 | 8.00 | 8.00 | 8.00 |
| PEG-120 Methyl Glucose Dioleate | 0.30 | 0.30 | 0.30 | 0.30 | 0.30 | 0.30 | 0.30 |
| Sodium Benzoate | 0.30 | 0.30 | 0.30 | 0.30 | 0.30 | 0.30 | 0.30 |
| CI 77891 (Titanium Oxide) & CI 77491 (Iron Oxide) % Mica | 0.30 | 0.30 | 0.30 | 0.30 | 0.30 | 0.30 | 0.30 |
| Perfume (Fragrance) | 0.50 | 0.50 | 0.50 | 0.50 | 0.50 | 0.50 | 0.50 |
| PEG-40 Hydrogenated Castor Oil | 0.50 | 0.50 | 0.50 | 0.50 | 0.50 | 0.50 | 0.50 |
| Water | 10.00 | 10.00 | 10.00 | 10.00 | 10.00 | 10.00 | 10.00 |
| Polyquaternium-10 | 0.40 | 0.40 | 0.40 | 0.40 | 0.40 | 0.40 | 0.40 |
| Citric Acid | 0.75 | 0.75 | 0.75 | 0.75 | 0.75 | 0.75 | 0.75 |
| Sodium Chloride | 0.80 | 0.80 | 0.80 | 0.80 | 0.80 | 0.80 | 0.80 |
| Addition | | | | | | | |
| Water | | 10.00 | 9.00* | 6.00 | 8.00 | 6.00 | 8.00 | 6.00 |
| Hydrogenated Castor Oil | | | 0.20** | | | | | |
| PEG-7 Glyceryl Cocoate | | | 0.80** | | | | | |
| Ex. 1 | | | | 4.00 | | | | |
| Ex. 2 | | | | | 2.00 | | | |
| Ex. 3 | | | | | | 4.00 | | |
| Ex. 4 | | | | | | | 2.00 | |
| Ex. 5 | | | | | | | | 4.00 |
| Total | 90 | 100 | 100 | 100 | 100 | 100 | 100 |

*In the case of stabilization with hydrogenated castor oil, the 9 parts water were first heated to 80° C.
**Hydrogenated castor oil and PEG-7 glyceryl cocoate were melted together at 85° C. and added to the water heated to 85° C.

TABLE 3-continued

Stability tests

| | Storage temperature | Evaluation |
|---|---|---|
| Stabilization with Ex. 2 | 45° C. | No change |
| | 50° C. | No change |
| Stabilization with Ex. 3 | 45° C. | No change |
| | 50° C. | No change |
| Stabilization with Ex. 4 | 45° C. | No change |
| | 50° C. | No change |
| Stabilization with Ex. 5 | 45° C. | No change |
| | 50° C. | Slight separation |

Therefore, it has been demonstrated that a clear improvement of stability is achieved at increased temperatures if the stabilization mixtures as contemplated herein are added cold to a base shampoo.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An aqueous dispersion of hydrogenated castor oil for stabilization of aqueous surfactant agents comprising pearlescent waxes and/or pearlescent pigments, which, relative to the total weight of the aqueous dispersion, comprises:
  (a) from 5 to 10 wt. % hydrogenated castor oil,
  (b) from 2.5 to 3.75 wt. % sodium laureth sulfate,
  (c) from 6 to 15 wt. % of one or more amphoteric surfactants selected from the group of cocamidopropyl hydroxysultaine and cocamidopropyl betaine, and
  (d) from 7.5 to 15 wt. % of one or more nonionic surfactants selected from the group of laureth-4, PEG-40 hydrogenated castor oil, and PEG-7 glyceryl cocoate, wherein no visual separation is observed after 5 days of storage at 45° C. when the aqueous dispersion is added to a base shampoo.

2. The aqueous dispersion according to claim 1, wherein the aqueous dispersion does not contain any cationic surfactant.

3. A method for production of a stabilized surfactant-containing aqueous agent having a pearlescent effect, the method comprising introducing the aqueous dispersion according to claim 1 to a surfactant-containing aqueous agent comprising pearlescent wax and/or pearlescent pigments in a cold process to obtain a stabilized surfactant-containing aqueous agent.

4. The method according to claim 3, wherein the end concentration of hydrogenated castor oil in the stabilized surfactant-containing aqueous agent is 0.1 to 1 wt. %.

5. The method according to claim 3, wherein the end concentration of hydrogenated castor oil in the stabilized surfactant-containing aqueous agent is 0.2 to 0.5 wt. %.

6. An aqueous dispersion of hydrogenated castor oil for stabilization of aqueous surfactant agents comprising pearlescent waxes and/or pearlescent pigments, which, relative to the total weight of the aqueous dispersion, consists essentially of:
  (a) from 5 to 10 wt. % hydrogenated castor oil,
  (b) from 2.5 to 3.75 wt. % sodium laureth sulfate,
  (c) from 6 to 15 wt. % of one or more amphoteric surfactants selected from the group of cocamidopropyl hyroxysultaine and cocamidopropyl betaine,
  (d) from 7.5 to 15 wt. % of one or more nonionic surfactants selected from the group of laureth-4, PEG-40 hydrogenated castor oil, and PEG-7 glyceryl cocoate,
  (e) water, and optionally (f) sodium benzoate and/or (g) citric acid, wherein no visual separation is observed after 5 days of storage at 45° C. when the aqueous dispersion is added to a base shampoo.

7. The aqueous dispersion according to claim 6, wherein the water is present in an amount of from 40 to 90 wt. % relative to the total weight of the aqueous dispersion.

8. The aqueous dispersion according to claim 6, wherein the sodium benzoate is present in an amount of 0.50 wt. % relative to the total weight of the aqueous dispersion.

9. The aqueous dispersion according to claim 6, wherein the citric acid is present in an amount of 0.25 wt. % relative to the total weight of the aqueous dispersion.

10. The aqueous dispersion according to claim 1, wherein the aqueous dispersion further comprises water in an amount of from 40 to 90 wt. % relative to the total weight of the aqueous dispersion.

11. The aqueous dispersion according to claim 1, wherein the aqueous dispersion further comprises sodium benzoate in an amount of 0.50 wt. % relative to the total weight of the aqueous dispersion.

12. The aqueous dispersion according to claim 1, wherein the aqueous dispersion further comprises citric acid in an amount of 0.25 wt. % relative to the total weight of the aqueous dispersion.

13. The aqueous dispersion according to claim 1, wherein the aqueous dispersion has a pH value of from 4.5 to 5.5.

* * * * *